United States Patent
Lim et al.

(10) Patent No.: US 10,799,503 B2
(45) Date of Patent: Oct. 13, 2020

(54) METHODS FOR THE TREATMENT OF CANCER

(71) Applicant: IGNYTA, INC., South San Francisco, CA (US)

(72) Inventors: Jonathan Ee-Ren Lim, San Diego, CA (US); Pratik S. Multani, San Diego, CA (US); Richard Landin, San Diego, CA (US); Rupal Patel, San Diego, CA (US); Jennifer Wright Oliver, San Diego, CA (US)

(73) Assignee: IGNYTA, INC., South San Francisco, CA (US)

( * ) Notice: Subject to any disclaimer, the term of this patent is extended or adjusted under 35 U.S.C. 154(b) by 0 days.

(21) Appl. No.: 16/466,005

(22) PCT Filed: Nov. 29, 2017

(86) PCT No.: PCT/US2017/063779
§ 371 (c)(1),
(2) Date: May 31, 2019

(87) PCT Pub. No.: WO2018/102455
PCT Pub. Date: Jun. 7, 2018

(65) Prior Publication Data
US 2020/0069688 A1    Mar. 5, 2020

Related U.S. Application Data

(60) Provisional application No. 62/428,947, filed on Dec. 1, 2016.

(51) Int. Cl.
*A61K 31/517* (2006.01)
*A61P 35/04* (2006.01)

(52) U.S. Cl.
CPC ............ *A61K 31/517* (2013.01); *A61P 35/04* (2018.01)

(58) Field of Classification Search
CPC ................................ C12Q 1/68; A61K 31/517
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 4,728,743 A | 3/1988 | Drauz et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,612,059 A | 3/1997 | Cardinal et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,698,220 A | 12/1997 | Cardinal et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,840,674 A | 11/1998 | Yatvin et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,972,366 A | 10/1999 | Haynes et al. | |
| 5,972,891 A | 10/1999 | Kamei et al. | |
| 5,980,945 A | 11/1999 | Ruiz | |
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |

(Continued)

FOREIGN PATENT DOCUMENTS

| CN | 102026985 A | 4/2011 |
|---|---|---|
| EP | 2 902 029 A1 | 8/2015 |

(Continued)

OTHER PUBLICATIONS

"Investor Conference Call: Program Highlights at 2016 EORTC-NCI-AACR(ENA) Molecular Targets and Cancer Therapeutics Symposium", Ignyta, Dec. 1, 2016, 43 slides.

(Continued)

*Primary Examiner* — Paul V Ward
(74) *Attorney, Agent, or Firm* — Foley & Lardner LLP

(57) ABSTRACT

Disclosed herein are methods of treating cancer in a subject, wherein the subject is known to possess at least one genetic alteration in RET, comprising administering to the subject a therapeutically effective amount of N-[3-[(6,7-dimethoxy-4-quinazolinyl)oxy]phenyl]-N'-[5-(2,2,2-trifluoro-1, 1-dimethylethyl)-3-isoxazolyl]-urea, or a pharmaceutically acceptable salt thereof.

13 Claims, 3 Drawing Sheets

(56) References Cited

U.S. PATENT DOCUMENTS

| | | | |
|---|---|---|---|
| 6,139,865 | A | 10/2000 | Friend et al. |
| 6,143,764 | A | 11/2000 | Kubo et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,350,458 | B1 | 2/2002 | Modi |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,797,823 | B1 | 9/2004 | Kubo et al. |
| 6,821,987 | B2 | 11/2004 | Kubo et al. |
| 7,135,466 | B2 | 11/2006 | Sakai et al. |
| 7,169,789 | B2 | 1/2007 | Kubo et al. |
| 7,211,587 | B2 | 5/2007 | Kubo et al. |
| 7,253,286 | B2 | 8/2007 | Funahashi et al. |
| 7,262,201 | B1 | 8/2007 | Hennequin et al. |
| 7,579,473 | B2 | 8/2009 | Bannen et al. |
| 7,750,160 | B2 | 7/2010 | Milanov et al. |
| 8,618,289 | B2 | 12/2013 | Abraham et al. |
| 8,969,587 | B2 | 3/2015 | Abraham et al. |
| 9,320,739 | B2 | 4/2016 | Abraham et al. |
| 9,353,097 | B2 | 5/2016 | Bierlmaier et al. |
| 9,718,810 | B2 | 8/2017 | Bierlmaier et al. |
| 10,053,430 | B2 | 8/2018 | Sunny et al. |
| 2003/0087907 | A1 | 5/2003 | Kubo et al. |
| 2004/0242603 | A1 | 12/2004 | Fujiwara et al. |
| 2005/0165024 | A1 | 7/2005 | Milanov et al. |
| 2005/0165031 | A1 | 7/2005 | Grotzfeld et al. |
| 2005/0192314 | A1 | 9/2005 | Mehta et al. |
| 2005/0197371 | A1 | 9/2005 | Milanov et al. |
| 2005/0267182 | A1 | 12/2005 | Milanov et al. |
| 2006/0069077 | A1 | 3/2006 | Rice et al. |
| 2006/0142570 | A1 | 6/2006 | Herz et al. |
| 2007/0021446 | A1 | 1/2007 | Ehlert et al. |
| 2007/0185324 | A1 | 8/2007 | De Morin et al. |
| 2007/0244120 | A1 | 10/2007 | Dumas et al. |
| 2009/0227598 | A1 | 9/2009 | Buser-Doepner et al. |
| 2011/0201598 | A1 | 8/2011 | Gujral et al. |
| 2014/0243390 | A1 | 8/2014 | Downing et al. |
| 2015/0376171 | A1 | 12/2015 | Bierlmaier et al. |
| 2016/0009785 | A1 | 1/2016 | Lipson et al. |
| 2016/0199375 | A1 | 7/2016 | Abraham et al. |
| 2016/0280698 | A1* | 9/2016 | Bierlmaier ............ C07D 413/12 |

FOREIGN PATENT DOCUMENTS

| | | | |
|---|---|---|---|
| JP | 2011-529021 | | 12/2011 |
| SG | 191678 | A1 | 7/2013 |
| WO | WO-97/17329 | | 5/1997 |
| WO | WO-00/43366 | | 1/2000 |
| WO | WO-02/17918 | | 3/2001 |
| WO | WO-02/088110 | | 4/2002 |
| WO | WO-2004/006846 | A2 | 1/2004 |
| WO | WO-2005/037285 | | 4/2005 |
| WO | WO-2006/071940 | A2 | 7/2006 |
| WO | WO-2007/071963 | A2 | 6/2007 |
| WO | WO-2007/103370 | | 9/2007 |
| WO | WO-2007/113557 | A1 | 10/2007 |
| WO | WO-2007/113558 | A2 | 10/2007 |
| WO | WO-2008/005310 | | 1/2008 |
| WO | WO-2008/051493 | A2 | 5/2008 |
| WO | WO-2008/051494 | | 5/2008 |
| WO | WO-2009/117080 | A1 | 9/2009 |
| WO | WO-2011/050069 | A1 | 4/2011 |
| WO | WO-2012/053606 | A1 | 4/2012 |
| WO | WO-2012/138783 | A2 | 10/2012 |
| WO | WO-2013/018882 | A1 | 2/2013 |
| WO | WO2013/163428 | * | 10/2013 ............... C12Q 1/68 |
| WO | WO-2013/163428 | A1 | 10/2013 |
| WO | WO-2014/130975 | A1 | 8/2014 |
| WO | WO-2014/164648 | | 10/2014 |
| WO | WO-2005/030140 | | 4/2015 |

OTHER PUBLICATIONS

Adeyeye, ed., Preformulation in Solid Dosage Form Development (Informa Healthcare, 2008) Chapter 2.3, pp. 63-80.

Ballard, et al., Bioorganic & Medicinal Chemistry Letters, 16, 1633-1637, 2006.

Bastin et al., Organic Process Research & Development 2000, 4,427-435.

Brose, et al., Cancer Res., 62, 6997-7000, 2002.

Davies, et al., Nature, 417, 949-954, 2002.

Dong, et al., Annu. Re. Immunol., 20, 55-72, 2002.

Drilon et al., "A Phase 2 Single Arm Trial of Cabozantinib in Patients with Advanced RET-Rearranged Lung Cancers", The Lancet Oncology, 2016, 17(12):1653-1660.

Eddington, et al., Eur. J. Med. Chem., 37, 635-648, 2002.

Fabian, et al., Nature Biotechnology 23, 329-336, 2005.

Fecher, et al.. J. Clin. Oncology, 25 (12), 1606-1620, 2007.

Foster, et al., Adv. Drug Res., vol. 14, 1-36, 1985.

Garnett, et al., Cancer Cell, 6, 313-319, 2004.

Gatley, et al., J. Nucl. Med., 27:388, 1986.

Gordon, et al., Drug Melab. Dispos., 15: 589, 1987.

Gould, International J. of Therapeutics, 33, pp. 201-213 & 217 (1986).

Greenman, et al., Nature 226 (7132), 153-158, 2007.

Gura et al., Systems for Identifying new drugs are often faulty, Science, 278:1041-1042, 1997.

Haluska, et al., Clin. Cancer Res. 12 (7 PI 2), 2301 s-2307s, 2006.

Herrera, et al., Trends Mal. Med., 8, S27-S3, 2002.

Hofman, et al., Curr. Drug Targets, Inflamm. Allergy, (v3) 2004.

Holladay et al., 4-quinazolinyloxy-dlaryl ureas as novel BRAFv600E inhibitors, Biooganic & Medicinal Chemistry Letters, 2011, 21 :5342-5346.

Hoshino, et al., Oncogene, 18, 813-822, 1999.

Ikediobi, et al., Mal. Cancer Ther., 5 (11 ), 2606-2612, 2006.

James et al., "CEP-32496, A Novel Orally Active BRAFV600E Inhibitor with Selective Cellular and In Vivo Antitumor Activity," Mol Cancer Ther., (2012), 11(4):930-941.

Ji, et al., Cancer Res. 67 (10), 4933-4939, 2007.

Johnson et al., Relationships between drug activity in NCI preclinical in vitro and in vivo models and early clinical trials, British Journal of Cancer, 84(10):1424-1431,2001.

Johnson, et al., Curr. Opin. Chem. Biol., 9, 325-331, 2005.

Kushner, et al., Can. J. Physiol. Pharmacol., vol. 77, 79-88, 1999.

Kyriakis, et al., Physiol. Rev., 81, 807-869, 2001.

Lijinsky, et al., Food Cosmet. Toxicol., 20: 393, 1982.

Lijinsky, et al., J. Nat. Cancer Inst., 69: 1127, 1982.

Liu, ed., Water-insoluble Drug Formulation: Pharmaceutical Salts, Chapter 15, pp. 417-435, (2008).

Lowinger, et al., "Design and Discovery of Small Molecules Targeting Raf-1 Kinase," Current Pharmaceutical Design, (2002), 8:2269-2278.

Mangold, et al., Mutation Res. 308: 33, 1994.

McMahon, The Oncologist, 2000; 5(suppl. 1):3-10.

Melillo, etal., Clin. Invest., 115, 1068-1081, 2005.

Monia et al., Jun. 1996, Antitumor activity of a phosphorothioate antisense oligodeoxynucleotide targeted against C-raf kinase, Nature Medicine, 2(6):668-675.

Morris et al., International Journal of Pharmaceutics 105 (1994) 209-217.

Nakamura, et al., Cancer Res. 66, (18), 9134-9142, 2006.

Organic Compound Crystal Preparation Handbook—Theory and Know-how-, Maruzen Co., Ltd., Jul. 25, 2008, pp. 57-84.

Ouyang, et al., Clin. Cancer Res. 12 (6), 1785-1793, 2006.

PCT International Search Report and Written Opinion for PCT/ US2017/063779 dated Feb. 26, 2018. (16 pages).

(56) References Cited

OTHER PUBLICATIONS

Pearce et al., Failure modes in anticancer drug discovery and development, Cancer Drug Design and Discovery Edited by Stephen Neidle, Chapter 18, pp. 424-435 (2008).
Pinedo et al., The Oncologist, 2000; 5(suppl. 1):1-2.
Rowbottom et al., Identification of 1-(3-(6,7-Dimethoxyquinazolin-4-yloxy)phenyl)-3-(5-(1,1,1-trifluoro-2-methylpropan-2-yl)isoxazol-3-yl)urea Hydrochloride (CEP-32496), a Highly Potent and Orally Efficacious Inhibitor of V-RAF Murine Sarcoma Viral Oncogene Homologue 81 (BRAF) V600E, J Med Chem., 55, pp. 1082-1105 (published: Dec. 14, 2011 ).
Sabari et al., "Targeting RET-rearranged lung cancers with multikinase inhibitors", Oncoscience, 2017, 4(3-4):23-24.
Saito et al., "A mouse model of KIF5B-RET fusion-dependent lung tumorigenesis", Carcinogenesis, 2014, 35(11):2452-2456.
Santus and Baker, J. Controlled Release, 35, pp. 1-21, 1995.
Sawatzky, et al., Am. J. Pathol. 168 (1), 33-41, 2006.
Serajuddin, Advanced Drug Delivery Reviews 59 (2007) 603-616.
Sharma, et al., Cancer Res., (66) 16, 8200-8209, 2006.
Sharma, et al., Cancer Res., 65 (6), 2412-2421, 2005.
Simone, Oncology: Introduction, Cecil Textbook of Medicine, 20th Edition, vol. 1, pp. 1004-1010, 1995.
Stahl, P.H. et al., "Handbook of Pharmaceutical Salts: Properties, Selection, and Use," Wiley-VCH, Zurich, 2008, pp. 265-327.
Stanton, et al., Dev. Biol., 263, 165-175, 2003.
Still, et al., J. Org. Chem. 43:2923-5, 1978.
Swarbrick et al., eds. Encyclopedia of Pharmaceutical Technology 13 (Marcel Dekker, NY 1996) pp. 453-499.
Takase, et al., Heterocycles, 32(6), 1153-1158, 1991.
Takase, et al., J. Med. Chem, 37, 2106-2111, 1994.
Takata, Drug Form Screening and Selection at Drug Development Stage, Pharm Stage, Jan. 15, 2007, vol. 6, No. 10, pp. 20-25.
Thaimattam, et al., "3D-QSAR CoMFA, CoMSIA studies on substituted ureas as Raf-1 kinase inhibitors and its confirmation with structure-based studies," Bioorg. & Med. Chem., (2004), 12:6415-6425.
Verma, et al., Drug Development and Industrial Pharmacy, 26, pp. 695-708, 2000.
Verma, et al., J. Controlled Release, 79, pp. 7-27, 2002.
Wade, D., Chem. Biol, Interact. 117: 191, 1999.
Wan, et al., Cell 116, 855-867, 2004.
Wang et al., "RET Fusions Define a Unique Molecular and Clinicopathologic Subtype of Non-Small-Cell Lung Cancer", Journal of Clinical Oncology, 2012, 30(35):4352-4359.
Wermuth, New Drug-Creating Chemistry, Last Volume, Technomic Publishing Co., Inc., 1999, 347-365.
Wilhelm, et al., Nat. Rev. Drug. Discov., 5, 835-844, 2006.
Zello, et al., Metabolism, 43:487, 1994.
Zitzelsberger et al., "Chromosomal aberrations in thyroid follicular-cell neoplasia: in the search of novel oncogenes and tumour suppressor genes", Molecular and Cellular Endocrinology, Elsevier, 2010, 321(1):57. https://hal.archives-ouvertes.fr/hal-00582106.

\* cited by examiner

METHODS FOR THE TREATMENT OF CANCER

CROSS REFERENCE TO RELATED APPLICATIONS

This application claims the benefit of and priority to U.S. Provisional Patent Application No. 62/428,947, filed Dec. 1, 2016, the content of which is hereby incorporated by reference herein in its entirety.

FIELD OF THE INVENTION

The present invention relates to the treatment of subjects having cancer, comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

BACKGROUND OF THE INVENTION

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3:459-465.

The RET proto-oncogene encodes a receptor tyrosine kinase for members of the glial cell line-derived neurotrophic factor (GDNF) family of extracellular signalling molecules. Loss or RET mutations are associated with the development of Hirschsprung's disease, while gain of function mutations are associated with the development of various types of human cancer, including medullary thyroid carcinoma. Rearrangement of the proto-oncogene rearranged during transfection (RET) has been newly identified potential driver mutation in cancers, including lung adenocarcinoma. As such, there is a need to develop new modalities for the treatment of subjects having cancer with inhibitors of RET.

SUMMARY OF THE INVENTION

Disclosed herein are methods of treating cancer in a subject, wherein said subject is known to possess at least one genetic alteration in RET, comprising administering to said cancer subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

DETAILED DESCRIPTION

Figure 1:
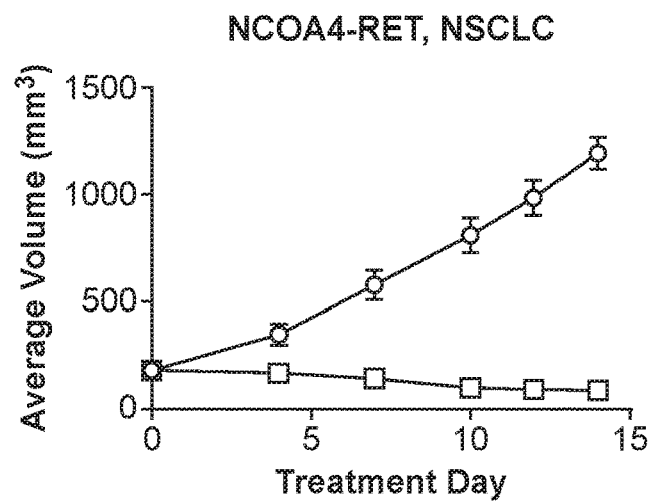
FIG. 1 is a view of three plots showing plots from experiments described in Example 1 in which animals that had been implanted with cells having the indicated RET fusion genes with N-[3-[(6,7-dimethoxy-4-quinazolinyl)oxy]phenyl]-N'-[5-(2,2,2-trifluoro-1,1-dimethylethyl)-3-isoxazolyl]-urea at a dose of 30 mg/kg BID (squares) versus vehicle (circles). Circles represent dosing with vehicle; squares represent dosing in mice that have been implanted with cells having the indicated RET fusion genes with N-[3-[(6,7-dimethoxy-4-quinazolinyl)oxy]phenyl]-N'-[5-(2,2,2-trifluoro-1,1-dimethylethyl)-3-isoxazolyl]-urea at a dose of 30 mg/kg BID.
Figure 1:
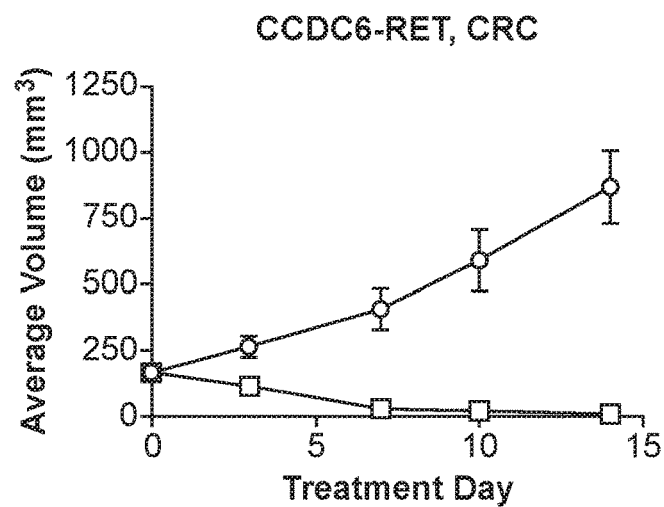
Figure 1:
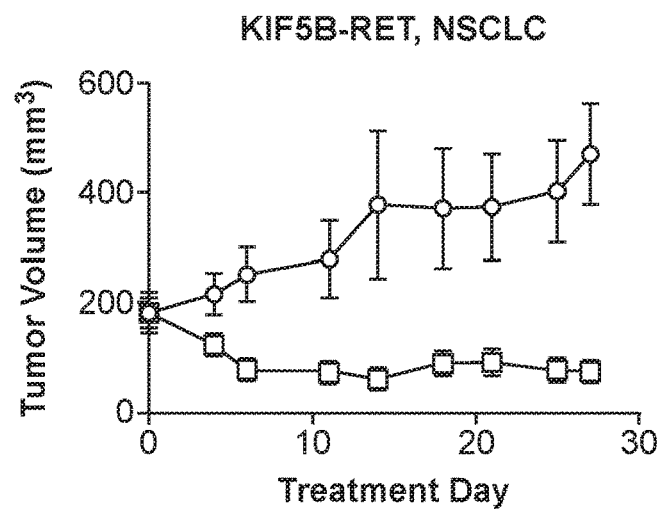

The term "N-[3-[(6,7-dimethoxy-4-quinazolinyl)oxy]phenyl]-N'-[5-(2,2,2-trifluoro-1,1-dimethylethyl)-3-isoxazolyl]-urea" means a compound having the chemical structure

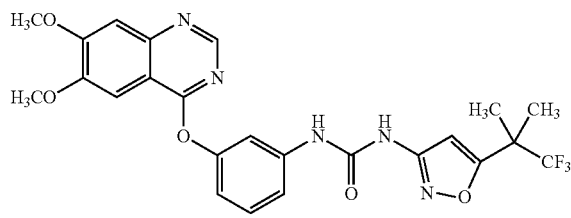 [SMILES: COc1cc2ncnc(Oc3cccc(NC(=O)Nc4cc(C(C)(C)C(F)(F)F)on4)c3)c2cc1OC]

The compound is alternatively named as 1-[3-[(6,7-dimethoxyquinazolin-4-yl)oxy]phenyl]-3-[5-(1,1,1-trifluoro-2-methylpropan-2-yl)isoxazol-3-yl]urea, and has been assigned Chemical Abstracts Registry No. 1188910-76-0. The compound may also be referred to herein as "RXDX-105." The preparation of the compound is disclosed in U.S. Pat. No. 8,618,289, the disclosure of which is incorporated herein by reference in its entirety.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B". The term "about," as used herein, means either within plus or minus 10% of the provided value, or rounded to the nearest significant figure, in all cases inclusive of the provided value. Where ranges are provided, they are inclusive of the boundary values.

The terms "administration" and "administering", as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof.

The term "at least one genetic alteration," as used herein, means any variation in the genetic or protein sequence in or more cells of a subject as compared to the corresponding wild-type genes or proteins. One or more molecular alterations include, but are not limited to, genetic mutations, gene amplifications, splice variants, deletions, insertions/deletions, gene rearrangements, single-nucleotide variations (SNVs), insertions, and aberrant RNA/protein expression.

The term "cancer," as used herein, refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

The terms "combination" and "in combination with," as used herein, mean the administration of a therapeutic agent described herein together with at least one additional pharmaceutical or medicinal agent (e.g., an anti-cancer agent), either sequentially or simultaneously. For example, the term encompasses dosing simultaneously, or within minutes or hours of each other, or on the same day, or on alternating days, or dosing the therapeutic agent described herein on a daily basis, or multiple days per week, or weekly basis, for example, while administering another compound such as a chemotherapeutic agent on the same day or alternating days or weeks or on a periodic basis during a time simultaneous therewith or concurrent therewith, or at least a part of the time during which the therapeutic agent described herein is dosed.

The term "contact," as used herein in reference to specificity or specific binding means two molecules are close enough so that short range non-covalent chemical interactions, such as Van der Waal forces, hydrogen bonding, hydrophobic interactions, and the like, dominate the interaction of the molecule.

The term "pharmaceutically acceptable salt," as used herein, means those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like; salts formed when an acidic proton present in a compound is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

The term "RET," when used in herein in relation to a gene means the gene known to those having ordinary skill in the art as the Ret Proto-Oncogene. Alternative names for the RET gene that are known to those having ordinary skill in the art include CDHF12, CDHR16, PTC, and RET51. The term "RET," when used herein in relation to a protein means the wild-type protein known to those having ordinary skill in the art as RET and having UniProt identifier RET_HUMAN (P07949).

Disclosed herein are methods of treating cancer in a subject, wherein said subject is known to possess at least one genetic alteration in RET, comprising administering to said cancer subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

In one embodiment, said at least one genetic alteration in RET is a gene fusion or an activating point mutation.

In one embodiment, said at least one genetic alteration in RET is an activating point mutation. In one embodiment, said activating point mutation is an M918T point mutation.

In one embodiment, said at least one genetic alteration in RET is a gene fusion. In one embodiment, said gene fusion is selected from a NCOA4-RET, a KIF5B-RET fusion, a CCDC6-RET fusion, an EML4-RET fusion, and a PARD3-RET fusion. In one embodiment, the gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

In one embodiment, said at least one genetic alteration in RET is a gene fusion. In one embodiment, said gene fusion is selected from a NCOA4-RET, a KIF5B-RET fusion, a CCDC6-RET fusion, an EML4-RET fusion, a PARD3-RET fusion, and a CLIP1-RET fusion. In one embodiment, the gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion.

In one embodiment, are provide methods of treating a subject having cancer, wherein the cancer is known to have at least one genetic in RET, comprising administering to said cancer subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In some embodiments the at least one genetic alteration in RET is a gene fusion. In one embodiment, said gene fusion is selected from a NCOA4-RET, a KIF5B-RET fusion, a CCDC6-RET fusion, an EML4-RET fusion, a PARD3-RET fusion, and a CLIP1-RET fusion. In one embodiment, the gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor.

In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion.

In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion.

In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion.

In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also provided herein are any of the methods described herein, wherein said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 900 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 800 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 700 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 600 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 500 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 400 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 375 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 150 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 175 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 200 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 225 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 175 mg to about 800 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 275 mg to about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 200 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 225 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 250 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 275 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 300 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 325 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 375 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 400 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 425 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 450 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 475 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 500 mg per day.

Also provided herein, are any of the methods described herein, wherein said subject is administered said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in the fed state.

Also provided herein, are any of the methods described herein, wherein said subject is RET-inhibitor naïve. Also provided herein, are any of the methods described herein, wherein said subject is not RET-inhibitor naïve.

Also provided herein, are any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor.

Some embodiments of the present invention, are to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and Pancreatic cancer.

Some embodiments of the present invention, are to treat specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, Pancreatic cancer, and medulloblastoma.

Some embodiments of the present invention, are to treat specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, Pancreatic cancer, and medulloblastoma. In some embodiments, the lung cancer is small cell lung cancer or non-small cell lung cancer. In some embodiments, the cancer is small cell lung cancer. In some embodiments, the cancer is non-small cell lung cancer.

Some embodiments of the present invention, are to treat, reduce the symptoms of, ameliorate the symptoms of, delay the onset of, or otherwise pharmaceutically address cancer in which a defect in the modulation of RET activity, or upregulation, misregulation or deletion thereof might play a role by administering a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

Also disclosed herein are methods to treat, reduce the symptoms of, ameliorate the symptoms of, delay the onset of, or otherwise pharmaceutically address cancer and possibly other indications in a subject in which a defect in the modulation of RET activity, or upregulation, misregulation or deletion thereof might play a role by administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

In some embodiments, methods of the present invention are to treat, reduce the symptoms of, ameliorate the symptoms of, delay the onset of, or otherwise pharmaceutically address cancer in a subject associated with a RET down-regulation defect, for example a null mutation such as a RET deletion by identifying a RET down-regulation defect, for example a null mutation such as a RET deletion in a cancer or precancerous cell in a subject, and administering to the subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

In some embodiments identifying a RET modulation defect such as an upregulation defect or a down-regulation defect, for example a null mutation such as a RET deletion or a RET chimeric locus encoding a constitutively active RET kinase in a cancer or precancerous pancreatic cell in an subject comprises assaying for RET activity in a cell extract from a pancreatic cancerous or precancerous cell population. In some embodiments identifying a RET modulation defect such as an upregulation defect or a down-regulation defect, for example a null mutation such as a RET deletion or a RET chimeric locus encoding a constitutively active RET kinase in a cancer or precancerous pancreatic cell in an subject comprises assaying for RET transcript accumulation in an RNA population from a pancreatic cancerous or precancerous cell population. In some embodiments identifying a RET modulation defect such as an upregulation defect or a down-regulation defect, for example a null mutation such as a RET deletion or a RET chimeric locus encoding a constitutively active RET kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments, the method of the present invention further comprises subjecting the subject having cancer to a radiation therapy or chemotherapy regimen in combination with at least one cytostatic or cytotoxic agent. Moreover the invention provides a method for inhibiting the activity RET protein which comprises contacting the said protein with an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

Also provided herein are methods for inhibiting RET kinase activity in a cell, comprising contacting said cell with an effective amount of effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

The present invention also provides a pharmaceutical composition comprising a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, and a pharmaceutically acceptable excipient, carrier or diluent.

Also disclosed herein are methods of inhibiting RET activity in a subject, comprising administering to said subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

Also disclosed herein are methods of treating cancer in a subject in need thereof, comprising inhibiting RET activity in said subject, by administering to said subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

Also disclosed herein are methods of treating cancer in a subject in need thereof, the method comprising inhibiting RET activity in said subject, by administering to said subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof.

Some embodiments provide methods of treating lung cancer, non-small cell lung cancer, thyroid cancer, medullary thyroid cancer, papillary thyroid cancer, neuroblastoma, pancreatic cancer or colorectal cancer in a subject, wherein said subject is known to possess at least one genetic alteration in RET, comprising administering to said subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Some embodiments provide methods of treating lung cancer, non-small cell lung cancer, thyroid cancer, medullary thyroid cancer, papillary thyroid cancer, neuroblastoma, pancreatic cancer or colorectal cancer in a subject, wherein said subject is known to possess at least one genetic alteration in RET, comprising administering to said subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1 fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion.

Also disclosed herein are methods of treating tumors in a subject, said methods comprising administering to the subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In one embodiment, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Also disclosed herein are methods of treating tumors in a subject, said methods comprising administering to the subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In one embodiment, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion.

Some embodiments provide methods wherein the tumors are caused by the presence of lung cancer, non-small cell lung cancer, thyroid cancer, meduallary thyroid cancer, papillary thyroid cancer, neuroblastoma, pancreatic cancer or colorectal cancer in the subject. Some embodiments provide methods wherein one or more of the cells comprising the tumors in the subject test positive for the presence of a gene that expresses RET or one or more of the cells comprising the tumors in said subject demonstrates RET activity.

Some embodiments provide methods wherein one or more of the cells comprising the tumors in the subject test positive for at least one gene rearrangement comprising RET, or a fragment thereof, that expresses RET.

Also disclosed herein are methods of treating cancer in a subject, the method comprising: (1) testing one or more cells comprising the tumors in the subject for the presence of RET; and (2) administering to the subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, if said one or more cells tests positive for RET. In one embodiment, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Also disclosed herein are methods of treating cancer in a subject, the method comprising: (1) testing one or more cells comprising the tumors in the subject for the presence of RET; and (2) administering to the subject an effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, if said one or more cells tests positive for RET. In one embodiment, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Some embodiments provide a method of treating a subject having cancer, comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein prior to said administration of said compound, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Some embodiments provide a method of treating a subject having cancer, comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein prior to said administration of said compound, said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also disclosed herein are methods for treating a cancer in a subject, comprising (a) acquiring knowledge of the presence of at least one genetic alteration in RET in one or more cells of said subject; and (b) administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Also disclosed herein are methods for treating a cancer in a subject, comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein prior to the administration of N-[3-[(6, 7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein the subject has been diagnosed as having a cancer comprising at least one genetic alteration in RET. In some embodiments, the at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also disclosed herein are methods for treating a cancer in a subject, comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein prior to the administration of N-[3-[(6, 7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein the subject has been previously diagnosed as having a cancer comprising at least one genetic alteration in RET. In some embodiments, the at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also disclosed herein are pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Also disclosed herein are a product or kit comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions thereof and one or more chemotherapeutic agents, as a combined preparation for simultaneous, separate or sequential use in anticancer therapy. Also disclosed herein are a product or kit comprising a compound which is N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions thereof and one or more chemotherapeutic agents, as a combined preparation for simultaneous, separate or sequential use in anticancer therapy.

Also disclosed herein is the use of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, for use as a medicament. In one embodiment, the medicament intended for use in a subject having cancer. In one embodiment said cancer in said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Also disclosed herein is the use of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, for use as a medicament. In one embodiment, the medicament intended for use in a subject having cancer. In one embodiment said cancer in said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also disclosed herein is the use of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in the manufacture of a medicament with antitumor activity. In one embodiment, the medicament intended for use in a subject having cancer. In one embodiment said cancer in said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, and PARD3-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion.

Also disclosed herein is the use of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in the manufacture of a medicament with antitumor activity. In one embodiment, the medicament intended for use in a subject having cancer. In one embodiment said cancer in said subject is known to possess at least one genetic alteration in RET. In one embodiment, said at least one genetic alteration in RET is a gene fusion or an activating point mutation. In one embodiment, said gene fusion is selected from a NCOA4-RET, KIF5B-RET, CCDC6-RET fusion, EML4-RET fusion, PARD3-RET fusion, and CLIP1-RET fusion. In one embodiment, said activating point mutation is an M918T point mutation. In one embodiment, said gene fusion is a NCOA4-RET fusion. In one embodiment, the gene fusion is a KIF5B-RET fusion. In one embodiment, said gene fusion is a CCDC6-RET fusion. In one embodiment, said gene fusion is an EML4-RET fusion. In one embodiment, said gene fusion is a PARD3-RET fusion. In one embodiment, said gene fusion is a CLIP1-RET fusion. In one embodiment are provided any of the methods described herein, wherein said cancer in said subject is selected from colorectal cancer, lung cancer, non-small cell lung cancer, thyroid cancer, and medullary thyroid cancer. In one embodiment, said cancer in said subject is colorectal cancer. In one embodiment, said colorectal cancer is metastatic colorectal cancer. In one embodiment, said cancer in said subject is lung cancer. In one embodiment, said cancer in said subject is non-small cell lung cancer. In one embodiment, said cancer in said subject is thyroid cancer. In one embodiment, said cancer in said subject is medullary thyroid cancer. In one embodiment, said cancer is said subject is a solid tumor or a liquid tumor. In one embodiment, said cancer in said subject is a solid tumor. In one embodiment, said cancer in said subject is a liquid tumor. In some embodiments, the subject is suffering from lung cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from lung cancer having at least one genetic alteration in RET, wherein the at least one genetic alteration is a CCDC6-RET fusion. In some embodiments, the subject is suffering from lung cancer having at least one genetic alteration in RET, wherein the at least one genetic alteration is an EML4-RET fusion. In some embodiments, the subject is suffering from lung cancer having at least one genetic alteration in RET, wherein the at least one genetic alteration is a PARD3-RET fusion. In some embodiments, the subject is suffering from lung cancer having at least one genetic alteration in RET, wherein the at least one genetic alteration is a CLIP1-RET fusion. In some embodiments, the subject is suffering from colorectal cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from colorectal cancer having at least one genetic alteration in RET, wherein the at least one genetic alteration is a CCDC6-RET fusion. In some embodiments, the subject is suffering from colorectal cancer having at least one genetic alteration in RET, wherein the at least one genetic alteration is an EML4-RET fusion. In some embodiments, the subject is suffering from colorectal cancer having at least one genetic alteration in RET, wherein the at least one genetic alteration is a PARD3-RET fusion. In some embodiments, the subject is suffering from colorectal cancer having at least one genetic alteration in RET, wherein the at least one genetic alteration is a CLIP1-RET fusion. In some embodiments, the subject is suffering from medullary thyroid cancer having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from medullary thyroid cancer having at least one genetic alteration in RET, wherein the at least one genetic alteration is a CCDC6-RET fusion. In some embodiments, the subject is suffering from medullary thyroid cancer having at least one genetic alteration in RET, wherein the at least one genetic alteration is an EML4-RET fusion. In some embodiments, the subject is suffering from medullary thyroid cancer having at least one genetic alteration in RET, wherein the at least one genetic alteration is a PARD3-RET fusion. In some embodiments, the subject is suffering from medullary thyroid cancer having at least one genetic alteration in RET, wherein the at least one genetic alteration is a CLIP1-RET fusion. In some embodiments, the subject is suffering from sarcoma having at least one genetic alteration in RET, wherein the at least one genetic alteration is a gene fusion is selected from a NCOA4-RET, a KIF5B-RET fusion, a CCDC6-RET fusion, an EML4-RET fusion, a PARD3-RET fusion, and a CLIP1-RET fusion. In some embodiments, the subject is suffering from sarcoma having at least one genetic alteration in RET, wherein the at least one genetic alteration is a CCDC6-RET fusion. In some embodiments, the subject is suffering from sarcoma having at least one genetic alteration in RET, wherein the at least one genetic alteration is an EML4-RET fusion. In some embodiments, the subject is suffering from sarcoma having at least one genetic alteration in RET, wherein the at least one genetic alteration is a PARD3-RET fusion. In some embodiments, the subject is suffering from sarcoma having at least one genetic alteration in RET, wherein the at least one genetic alteration is a CLIP1-RET fusion.

Also disclosed herein is the use of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, for use in a method of treating cancer. Some embodiments may be further summarized by reference to the numerically listed embodiments recited below:

1. A method of treating, ameliorating the symptoms of, delaying the onset of or delaying the progression of cancer comprising the steps of
determining whether modulation of RET activity is defective in a cell population of a subject, and if said modulation of RET activity is defective, administering N-[3-[(6,7-dimethoxy-4-quinazolinyl)oxy] phenyl]-N'-[5-(2,2,2-trifluoro-1,1-dimethylethyl)-3-isoxazolyl]-urea, or a pharmaceutically acceptable salt thereof, to said subject.

thereby treating, ameliorating the symptoms of, delaying the onset of or delaying the progression of cancer.

2. The method of embodiment 1, wherein said determining whether modulation of RET activity is defective comprises assaying for RET kinase activity in an extract of a cell population of said subject.

3. The method of embodiment 1, wherein said determining whether modulation of RET activity is defective comprises assaying for transcript accumulation in an extract comprising RNA of a cell population of said subject.

4. The method of embodiment 1, wherein said determining whether modulation of RET activity is defective comprises sequencing a RET locus in the genomic DNA of a cell population of said subject.

5. The method of embodiment 4, wherein said defective modulation of RET activity comprises upregulation of RET activity.

6. The method of embodiment 5, wherein a fusion of a coding region of a second protein at the RET locus indicates upregulation of RET kinase activity.

7. The method of embodiment 4, wherein said defective modulation of RET activity comprises a reduction of RET activity to a lower level.

8. The method of embodiment 7, wherein a null mutation of said RET locus indicates that RET activity is reduced.

9. The method of embodiment 7, wherein said null mutation comprises an insertion.

10. The method of embodiment 7, wherein said null mutation comprises a frame shift of a coding region encoding RET.

11. The method of embodiment 7, wherein said null mutation comprises a deletion within the locus encoding RET.

12. The method of embodiment 7, wherein said null mutation comprises a deletion of the nucleic acid sequence spanning the RET locus.

13. The method of embodiment 7, wherein a mutation affecting accumulation of RET mRNA indicates that RET activity is reduced.

Some embodiments include any of the methods described herein, wherein N-[3-[(6,7-dimethoxy-4-quinazolinyl)oxy] phenyl]-N'-[5-(2,2,2-trifluoro-1,1-dimethylethyl)-3-isoxazolyl]-urea, or a pharmaceutically acceptable salt thereof, is administered to said subject in an amount ranging from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$. Some embodiments include any of the methods described herein, wherein N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in an amount of about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$.

Some embodiments relate to compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof. Accordingly, in some embodiments, the invention relates to a pharmaceutical composition comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, a pharmaceutically acceptable carrier and, optionally, at least one additional medicinal or pharmaceutical agent. In some embodiments, the at least one additional medicinal or pharmaceutical agent is an anti-cancer agent as described below.

The pharmaceutically acceptable carrier may comprise a conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

In some embodiments, the composition comprises a therapeutically effective amount of a compound as disclosed herein and a pharmaceutically acceptable carrier.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound disclosed herein and an inert, pharmaceutically acceptable carrier or diluent.

To treat or prevent diseases or conditions mediated by RET, a pharmaceutical composition of the invention is administered in a suitable formulation prepared by combining a therapeutically effective amount (i.e., RET modulating, regulating, or inhibiting amount effective to achieve therapeutic efficacy) of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof (as an active ingredient), with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of N-[3-[(6,7-dimethoxy-4-quinazolinyl)oxy]phenyl]-N'-[5-(2,2,2-trifluoro-1,1-dimethylethyl)-3-isoxazolyl]-urea, may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be in powder form for constitution with a suitable vehicle, e.g. sterile pyrogen-free water, before use.

In addition to the formulations described above, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may also be formulated as a depot preparation. Such long-acting formulations may be administered by implantation (for example, subcutaneously or intramuscularly) or by intramuscular injection. Thus, for example, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Furthermore, the pharmaceutically acceptable formulations of the present invention may contain a compound of the present invention, or a salt or solvate thereof, in an amount of about 50 mg, about 100 mg, about 150 mg, about 200 mg, about 250 mg, about 300 mg, about 350 mg, about 400 mg, about 450 mg, or about 500 mg. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 900 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 800 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 700 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 600 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 500 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 400 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 375 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 150 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 175 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 200 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 225 mg to about 1000 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 175 mg to about 800 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 275 mg to about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 200 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 225 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 250 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 275 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 300 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 325 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 350 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 375 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 400 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 425 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 450 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 475 mg per day. In one embodiment, said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of about 500 mg per day.

Additionally, the pharmaceutically acceptable formulations of the present invention may contain N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

Also disclosed are any of the method methods disclosed herein, wherein the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, are administered to a subject suffering from cancer, either alone or as part of a pharmaceutically acceptable formulation, once a day, twice a day, three times a day, or four times a day, or even more frequently. In one embodiment, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject once per day. In one embodiment, N-[3-[(6,7-dimethoxy-4-quinazolinyl)oxy]phenyl]-

N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject twice per day. In one embodiment, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject three times per day. In one embodiment, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject four times per day. In one embodiment, N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject five times per day.

Also disclosed are any of the method methods disclosed herein, wherein the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, are administered to a subject suffering from cancer, either alone or as part of a pharmaceutically acceptable formulation, in either the fed state or the fasted state. In one embodiment, the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in the fed state. In one embodiment, the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in the fasted state.

Those of ordinary skill in the art will understand that with respect to the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, the particular pharmaceutical formulation, the dosage, and the number of doses given per day to a subject requiring such treatment, are all choices within the knowledge of one of ordinary skill in the art and can be determined without undue experimentation.

Administration of the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in subjects.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present invention.

It is to be noted that dosage values may vary with the type and severity of the condition to be alleviated, and may include single or multiple doses. It is to be further understood that for any particular subject, specific dosage regimens should be adjusted over time according to the subject need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-subject dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The compounds, compositions and methods provided herein are useful for the treatment of cancers including but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with the present invention include cancer selected from lung cancer (NSCLC and SCLC), cancer of the head or neck, ovarian cancer, colon cancer, rectal cancer, prostate cancer, cancer of the anal region, stomachcancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In some embodiments, the compounds and the compositions disclosed herein are useful for the treatment of cancers, including Spitz melanoma, perineural invasion, pulmonary large cell neuroendocrine carcinoma, uterine carcinoma, juvenile breast cancer, nasopharyngeal carcinoma, adenoid cystic cancer, meduallary thyroid cancer, salivary cancer, congenital infantile fibrosarcoma, mesoblastic nephroma, esophageal cancer (squamous), diffuse large B-cell lymphoma, papillary thyroid cancer, and mammary analogue secretory carcinoma.

In some embodiments, the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, may be used in combination with one or more additional anti-cancer agents which are described below. When a combination therapy is used, the one or more additional anti-cancer agents may be administered sequentially or simultaneously with the compound of the invention. In some embodiments, the additional anti-cancer agent is administered to a mammal (e.g., a human) prior to administration of the compound of the invention. In some embodiments, the additional anti-cancer agent is administered to the mammal after administration of the compound of the invention. In some embodiments, the additional anti-cancer agent is administered to the mammal (e.g., a human) simultaneously with the administration of the compound disclosed herein.

Some embodiments also relate to a pharmaceutical composition for the treatment of abnormal cell growth in a mammal, including a human, which comprises an amount of the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In some embodiments, the anti-cancer agent used in conjunction with a compound disclosed herein and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC.beta. inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, and pharmaceutical compositions described herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (Procyon).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®) squalamine (EVIZON®), thalidomide (Thalomid®), Ukrain® (NSC 631570), Vitaxin® (MEDI 522), and zoledronic acid (Zometa®)

In some embodiments, the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors which may be used in conjunction with a compound of Disclosed herein and pharmaceutical compositions described herein include BMS 214662 (Bristol-Myers Squibb), lonafarnib (Sarasar®), pelitrexol (AG 2037), matuzumab (EMD 7200), nimotuzumab (TheraCIM h-R3®), panitumumab (Vectibix®), Vandetanib (Zactima®), pazopanib (SB 786034), ALT 110 (Alteris Therapeutics), BIBW 2992 (Boehringer Ingelheim), and Cervene® (TP 38).

Other examples of signal transduction inhibitor include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), Neu-Vax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors include ARRY 142886 (Array Biopharm), everolimus (Certican®), zotarolimus (Endeavor®), temsirolimus (Torisel®), AP 23573 (ARIAD), and VX 680 (Vertex).

Additionally, other signal transduction inhibitors include XL 647 (Exelixis), sorafenib (Nexavar®), LE-AON (Georgetown University), and GI-4000 (GlobeImmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOXO-101 (Loxo Oncology), crizotinib, and ceritinib.

In some embodiments, the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2, 2,2-trifluoro-1,1-dimethylethyl)-3-isoxazolyl]-urea, or a pharmaceutically acceptable salt thereof, are used together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, episteride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, are used together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE—enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents used in combination therapy with the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Some embodiments relate to a method for the treatment of breast cancer in a human in need of such treatment, comprising administering to said human an amount of the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

Some embodiments provide a method of treating colorectal cancer in a mammal, such as a human, in need of such treatment, by administering an amount the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Some embodiments provide methods for the treatment of renal cell carcinoma in a human in need of such treatment, comprising administering to said human an amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Some embodiments provide methods for the treatment of melanoma in a human in need of such treatment, comprising administering to said human an amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, Axitinib, bevacizumab (Avastin), thalidomide, sorafanib, vatalanib (PTK-787), Sutent, CpG-7909, AG-13736, Iressa, Lapatinib and Gleevec, wherein the amounts of the active agent together with the amounts of the combination anticancer agents is effective in treating melanoma.

Some embodiments provide methods for the treatment of lung cancer in a human in need of such treatment, comprising administering to said human an amount of the N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, or pharmaceutical compositions comprising N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, in combination with one or more (preferably one to three) anti-cancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

Some embodiments provide methods for treating specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and Pancreatic cancer.

Some embodiments provide methods for treating specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, Pancreatic cancer, and medulloblastoma.

Molecular Screening

Transcript accumulation levels, genomic locus screening methods, and protein kinase activity assays for RET may be performed using methods known to one of skill in the art. Kinase assays may be performed by providing a substrate to a protein extract comprising RET. RET locus sequencing may be performed using, for example, whole genome shotgun sequencing, or targeted sequencing of the RET locus, for example through targeted amplification of the locus or a region spanning the locus wholly or in part, using PCR techniques know to one of skill in the art and primers generated through means known to one of skill in the art, followed by sequencing of any generated amplicons. Molecular alterations can be detected by next generation sequencing (NGS), quantitative reverse-transcription polymerase chain reaction DNA amplification reactions (qPCR), fluorescence in situ hybridization (FISH), and/or immunohistochemistry (IHC) and are inclusive of gene rearrangements, single-nucleotide polymorphisms (SNPs), insertions, deletions, splice variants, gene amplifications, and aberrant RNA/protein expression.

Copy number variations (CNVs), point mutations (SNPs/SNVs), insertions, deletions, gene rearrangements, RNA/protein over expression, and constitutive phosphorylation are measurable alterations that can result in oncogenic perturbation of RET, such as misregulation, upregulation, or downregulation through and including downregulation to complete loss of activity. A DNA-based test can detect CNVs, SNPs, insertions, deletions, and gene rearrangements. An RNA-based test can detect over expression, under expression (up to and including complete loss of expression) or misexpression of RET mRNA and many of the alterations detected in the DNA-based test. Protein-based tests allow one to measure the over expression, under expression (through and including complete loss of expression) or misexpression of RET protein; constitutive phosphorylation, constitutive dephosphorylation or misphosphorylation of the RET protein; and increase, decrease (through and including complete loss) or altered activity pattern of RET kinase activity.

Example 1: Administration of N-[3-[(6,7-dimethoxy-4-quinazolinyl)oxy]phenyl]-N'-[5-(2,2,2-trifluoro-1,1-dimethylethyl)-3-isoxazolyl]-urea to Mammals Implanted with Cells Having Various RET Gene Fusions Cells from subject-derived tumor samples having one of (a) a NCOA4-RET (colorectal cancer sample) gene fusion, (b) a CCDC6-RET gene fusion (colorectal cancer sample), or (c) a KIF5B-RET gene fusion (non-small cell lung cancer sample) were implanted in mice. The mice were then administered either vehicle or a preparation containing 30 mg/kg of N-[3-[(6,7-dimethoxy-4-quinazolinyl)oxy]phenyl]-N'-[5-(2,2,2-trifluoro-1,1-dimethylethyl)-3-isoxazolyl]-urea twice per day. Tumor volumes in the mice were measured on a regular basis.

FIG. 1 shows the results of the studies, wherein the average tumor volume in the mice ($mm^3$) are plotted on the y-axis and the number of treatment days are plotted on the x-axis. The tumors in the mice to which N-[3-[(6,7-dimethoxy-4-quinazolinyl)oxy]phenyl]-N'-[5-(2,2,2-trifluoro-1,1-dimethylethyl)-3-isoxazolyl]-urea were administered grew more slowly than the tumors in mice to which the vehicle were administered.

Example 2: Preparation of N-[3-[(6,7-dimethoxy-4-quinazolinyl)oxy]phenyl]-N'-[5-(2,2,2-trifluoro-1,1-dimethylethyl)-3-isoxazolyl]-urea hydrochloride To a reactor is added N-[3-[(6,7-dimethoxy-4-quinazolinyl)oxy]phenyl]-N'-[5-(2,2,2-trifluoro-1,1-dimethylethyl)-3-isoxazolyl]-urea free base and anhydrous tetrahydrofuran (THF). The reaction mixture is stirred and heated to approximately 45° C. and maintained at that temperature until a solution is obtained. After polish filtering the solution, a pre-formed, pre-filtered solution of hydrogen chloride in 2-propanol (IPA) is added at approximately 45° C., resulting in the precipitation of solids. The mixture is stirred at that temperature for a minimum of one hour. The mixture is cooled to approximately 0° C. and filtered. The filter cake is washed with pre-cooled THF, dried under vacuum and delumped to give N-[3-[(6,7-dimethoxy-4-quinazolinyl)oxy]phenyl]-N'-[5-(2,2,2-trifluoro-1,1-dimethylethyl)-3-isoxazolyl]-urea hydrochloride.

Example 3: Preparation of capsules comprising N-[3-[(6,7-dimethoxy-4-quinazolinyl)oxy]phenyl]-N'-[5-(2,2,2-trifluoro-1,1-dimethylethyl)-3-isoxazolyl]-urea hydrochloride Capsules comprising either 25 mg or 75 mg of N-[3-[(6,7-dimethoxy-4-quinazolinyl)oxy]phenyl]-N'-[5-(2,2,2-trifluoro-1,1-dimethylethyl)-3-isoxazolyl]-urea hydrochloride and the excipients in Tables 1 and 2, below, were prepared.

TABLE 1

| Ingredient | % w/w | Unit formula (mg/capsule) | Amount per Batch (g) (Batch size: 5,500 g) |
|---|---|---|---|
| N-[3-[(6,7-dimethoxy-4-quinazolinyl)oxy]phenyl]-N'-[5-(2,2,2-trifluoro-1,1-dimethylethyl)-3-isoxazolyl]-urea hydrochloride | 26.75* | 26.75[1] | 1471.25 |
| Hydroxypropyl-Betadex | 69.0 | 69.00 | 3795.00 |
| Sodium Starch Glycolate | 3.00 | 3.00 | 165.00 |
| Magnesium Stearate | 1.25 | 1.25 | 68.75 |
| Total | 100.00 | 100.00 | 5500.00 |
| Yellow HPMC Capsule Shell | NA | NA | NA |

(*26.75 mg of N-[3-[(6,7-dimethoxy-4-quinazolinyl)oxy]phenyl]-N'-[5-(2,2,2-trifluoro-1,1-dimethylethyl)-3-isoxazolyl]-urea HCl salt is equivalent to 25.00 mg of N-[3-[(6,7-dimethoxy-4-quinazolinyl)oxy]phenyl]-N'-[5-(2,2,2-trifluoro-1,1-dimethylethyl)-3-isoxazolyl]-urea free base per capsule)

TABLE 2

| Ingredient | % w/w | Unit formula (mg/capsule) | Amount per Batch (g) (Batch Size 17,700 g) |
|---|---|---|---|
| N-[3-[(6,7-dimethoxy-4-quinazolinyl)oxy]phenyl]-N'-[5-(2,2,2-trifluoro-1,1-dimethylethyl)-3-isoxazolyl]-urea hydrochloride | 26.75 | 80.25* | 4734.75 |
| Hydroxypropyl-betadex | 69.00 | 207.00 | 12213.00 |
| Sodium Starch Glycolate | 3.00 | 9.00 | 531.00 |
| Magnesium Stearate | 1.25 | 3.75 | 221.25 |
| Total | 100.00 | 300.00 | 17700.00 |
| White HPMC Capsule Shell (Size 0) | NA | NA | NA |

(*80.25 mg of N-[3-[(6,7-dimethoxy-4-quinazolinyl)oxy]phenyl]-N'-[5-(2,2,2-trifluoro-1,1-dimethylethyl)-3-isoxazolyl]-urea HCl salt is equivalent to 75.00 mg of N-[3-[(6,7-dimethoxy-4-quinazolinyl)oxy]phenyl]-N'-[5-(2,2,2-trifluoro-1,1-dimethylethyl)-3-isoxazolyl]-urea free base per capsule)

Screened N-[3-[(6,7-dimethoxy-4-quinazolinyl)oxy]phenyl]-N'-[5-(2,2,2-trifluoro-1,1-dimethylethyl)-3-isoxazolyl]-urea hydrochloride and a portion of magnesium stearate were mixed together. Hydroxypropyl-betadex and sodium starch glycolate (SSG), and the N-[3-[(6,7-dimethoxy-4-quinazolinyl)oxy]phenyl]-N'-[5-(2,2,2-trifluoro-1,1-dimethylethyl)-3-isoxazolyl]-urea hydrochloride/magnesium stearate premix were mixed into a suitable blender and blended. The blend was subsequently screened, blended and screened an additional time. The remaining portions of magnesium stearate were added to the mixture and the resulting mixture was blended. The final blend was sampled for blend uniformity. The appropriate capsules were filled using a capsule filling machine, followed by de-dusting, and the capsule weights were checked using an appropriate weight checker. The resulting capsules were then packaged into an appropriate container.

Example 4: Administration of N-[3-[(6,7-dimethoxy-4-quinazolinyl)oxy]phenyl]-N'-[5-(2,2,2-trifluoro-1,1-dimethylethyl)-3-isoxazolyl]-urea to Subjects Having Genetic Alterations in RET Phase I and Phase Ib clinical studies were performed in which 92 total subjects were enrolled, 91 of which were treated, and of which 35 in the Phase Ib portion were determined to be molecularly evaluable and were treated. Table 3 provides a summary of subject characteristics and disposition for those subjects that were enrolled in the Phase I and Phase Ib studies. Subjects were orally administered capsules comprising either 25 mg or 75 mg of N-[3-[(6,7-dimethoxy-4-quinazolinyl)oxy]phenyl]-N'-[5-(2,2,2-trifluoro-1,1-dimethylethyl)-3-isoxazolyl]-urea hydrochloride similar to those described in Example 3. The subjects received a starting dose that corresponded to a dose of 275 mg or 350 mg (calculated as the amount of free base) N-[3-[(6,7-dimethoxy-4-quinazolinyl)oxy]phenyl]-N'-[5-(2,2,2-trifluoro-1,1-dimethylethyl)-3-isoxazolyl]-urea once per day (QD), and the subjects were dosed in the fed state.

TABLE 3

| Subject Characteristics and Disposition, n (%) | |
|---|---|
| Total enrolled in Phase 1/1b | 92 (Phase 1: 55; Phase 1b: 37) |
| Total treated in Phase 1/1b | 91 (Phase 1: 55; Phase 1b: 36) |
| Total molecularly evaluable and treated in Phase 1b | 35 |
| Discontinued | 72 (78) |
| Primary reason for discontinuation | |
| Disease Progression | 49 (53) |
| Adverse Event Death | 11 (12) |
| Withdrawal by Subject | 4 (4) |
| Age, years, median (range) | 8 (7) |
| Sex, male/female % | 62 (27-83) |
| Number of prior anti-cancer therapies (median) | 56/44 |
| | 2.5 |

Table 4 provides a summary of the most common, treatment-related adverse events (AEs) in all patients that were treated (n=91), expressed as a percentage of the 91 patients.

TABLE 4

| | Grade ≤ 2 | Grade ≥ 3 | Any Grade |
|---|---|---|---|
| Rash* | 20 (22) | 8 (9) | 28 (31) |
| Fatigue | 16 (18) | 4 (4) | 20 (22) |
| Diarrhea | 14 (15) | 4 (4) | 18 (20) |
| Nausea | 16 (18) | 0 | 16 (18) |
| Hypophosphatemia | 7 (8) | 6 (7) | 13 (14) |
| Vomiting | 13 (14) | 0 | 13 (14) |
| Muscle Spasms | 12 (13) | 0 | 12 (13) |
| Decreased Appetite | 9 (10) | 0 | 9 (10) |
| Erythema | 7 (8) | 0 | 7 (8) |
| ALT increase | 1 (1) | 5 (6) | 6 (7) |
| Anemia | 5 (6) | 1 (1) | 6 (7) |
| AST increase | 3 (3) | 3 (3) | 6 (7) |
| Hypokalemia | 6 (7) | 0 | 6 (7) |
| Dysgeusia | 5 (6) | 0 | 5 (6) |

*includes 1 case of Grade 3 rash diagnosed as drug reaction with eosinophilia and systemic symptoms, in which the patient recovered with drug discontinuation, and one case of Grade 3 rash complicated by fatal alveolar hemorrhage Table 5 provides a summary of the 12 subjects enrolled in the Phase Ib study that were determined to have a RET fusion. Eight subjects were determined to be RET inhibitor-naïve and 4 subjects were determined not to be RET-inhibitor naïve

TABLE 5

| Evaluable Phase 1b Subjects, cancer type | Subjects that were RET inhibitor-naïve (n) | Subjects that were not RET inhibitor-naïve |
|---|---|---|
| RET fusion non-small cell lung cancer (NSCLC) | 7 | 2 |
| RET fusion metastatic colorectal cancer (mCRC) | 1 | N/A |
| RET mutated meduallary thyroid cancer | N/A | 1 |
| RET mutated sarcoma | N/A | 1 |
| Total | 8 | 4 |

Figure 2:
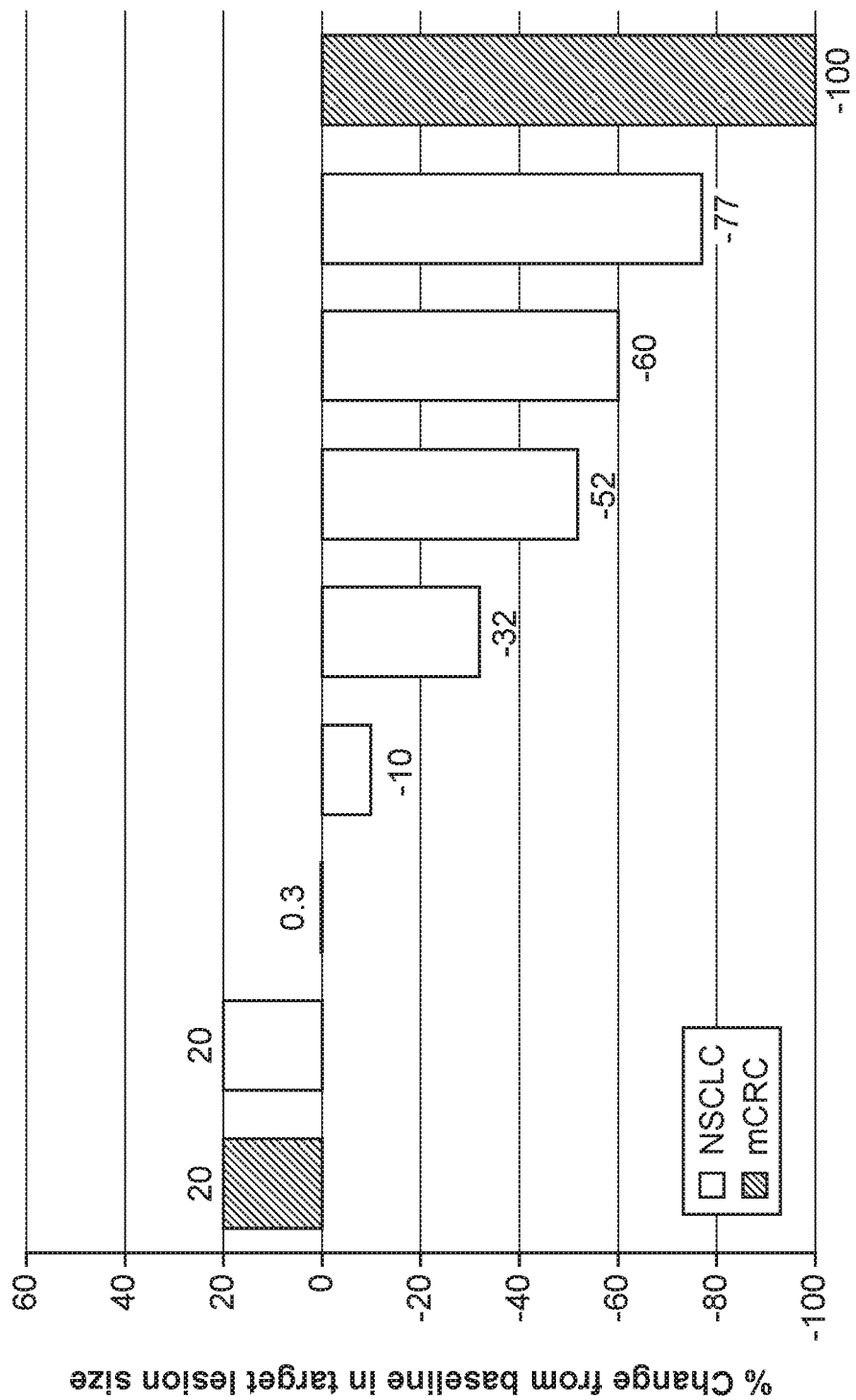
FIG. 2 is a waterfall plot showing the best tumor responses in RET-inhibitor naïve, RET fusion-positive subjects that took part in the Phase I and Phase Ib studies described in Example 4.

FIG. 2 is a waterfall plot showing the best tumor responses in RET-inhibitor naïve, RET fusion-positive subjects that took part in the Phase I and Phase Ib study. Note that FIG. 2 includes 8 subjects from the Phase Ib study and 1 subject from the Phase I study, which subject was determined to have a NCOA4-RET gene fusion and was suffering from metastatic colorectal cancer. The subjects received a starting dose that corresponded to a dose of 275 mg or 350 mg (calculated as the amount of free base) N-[3-[(6,7-dimethoxy-4-quinazolinyl)oxy]phenyl]-N'-[5-(2,2,2-trifluoro-1,1-dimethylethyl)-3-isoxazolyl]-urea once per day (QD), and the subjects were dosed in the fed state. In FIG. 2, the y-axis represents the percent change from baseline in the target lesion (tumor) size in each subject. Along the x-axis is plotted the details regarding individual subjects, including the specific genetic alteration the subject determined to have ("RET Fusion"), the duration of treatment ("DOT"), and the duration of response ("DOR"). The dotted lines labeled "PR" and "CR" are meant to represent the reduction in tumor size in a subject necessary under RECIST criteria to constitute a partial response ("PR") or a complete response ("CR"). The subjects having the responses labeled as 20, 0.3, (−10), (−32), (−52), (−60), and (−77) were suffering from non-small lung cancer (NSCLC). The subjects having the responses labeled as 20, and (−100) were suffering from metastatic colorectal cancer. In the study, the overall response rate of RET inhibitor naïve subjects determined to be RET fusion-positive was determined to be 56% (5 of 9 subjects).

Example 5: Administration of N-[3-[(6,7-dimethoxy-4-quinazolinyl)oxy]phenyl]-N'-[5-(2,2,2-trifluoro-1,1-dimethylethyl)-3-isoxazolyl]-urea to Subjects Having Genetic Alterations in RET Phase I and Phase Ib clinical studies were performed in which 152 total subjects were dosed with one more doses of N-[3-[(6,7-dimethoxy-4-quinazolinyl)oxy]phenyl]-N'-[5-(2,2,2-trifluoro-1,1-dimethylethyl)-3-isoxazolyl]-urea. Table 6 provides a summary of subject characteristics and disposition for those subjects that were enrolled in the Phase I and Phase Ib studies as of the data cut-off of Aug. 1, 2017. Of the 152 patients, 74 patients (49%) were orally administered 275 mg of the N-[3-[(6,7-dimethoxy-4-quinazolinyl)oxy]phenyl]-N'-[5-(2,2,2-trifluoro-1,1-dimethylethyl)-3-isoxazolyl]-urea compound in a pharmaceutical formulation once per day in the fed state.

TABLE 6

Patient Characteristics and Disposition, n (%)

| Dosing | Phase 1 (N = 55) | Phase 1b RET+ (N = 47) | Phase 1b Other (N = 50) | Total Subjects (N = 152) |
| --- | --- | --- | --- | --- |
| Dosing: Once per day in the fed state (275 mg Fed) | 12 (22) | 33 (70) | 29 (58) | 74 (49) |
| Dosing: Other | 43 (78) | 14 (30) | 21 (42) | 78 (51) |
| Number of patients still on treatment as of date of data cut-off | 2 | 27 | 4 | 33 |
| Total number of patients that discontinued treatment | 53 | 20 | 46 | 119 |
| Number that discontinued due to disease progression | 40 | 15 | 21 | 76 |
| Number that discontinued due to adverse vent | 7 | 1 | 11 | 19 |
| Number of patients that discontinued due to death | 3 | 0 | 1 | 4 |
| Number of patients that withdrew | 3 | 2 | 6 | 11 |
| Other (e.g., Investigator decision, lost to follow-up) | 0 | 2 | 7 | 9 |
| Age, years, median (range) | 61 (27, 81) | 61 (33, 79) | 69 (36, 90) | 63 (27, 90) |
| Sex, male/female % | 45/55 | 50/50 | 50/50 | 48/52 |
| Number of prior anti-cancer therapies, median (range) | 3 (1, 17) | 2 (0, 10) | 3 (0, 7) | 3 (0, 17) |

The majority of the treatment-related adverse events (AEs) were ≤Grade 2 and were reversible with dose modifications. Thirteen patients (9%) experienced 19 treatment-related serious adverse events (SAEs) and all except 1 resolved by dose modification or discontinuation. Toxicities commonly associated with VEGFR inhibition, such as hypertension, hypothyroidism, proteinuria, and neurotoxicity, were rarely observed. Administration of the compound under these conditions was not associated with QT/QTc prolongation. The most common (>10%) treatment related AEs as of the Aug. 1, 2017 data cut-off are presented in Table 7.

TABLE 7

| Adverse Event Term | Dose = 275 mg once per day fed (n = 74) | | Does = 350 mg once per day fed (n = 43) | | All Doses (n = 152) | |
| --- | --- | --- | --- | --- | --- | --- |
| | ≤G2 | ≥G3 | ≤G2 | ≥G3 | ≤G2 | ≥G3 |
| Rash* | 16 (22) | 9 (12) | 11 (26) | 6 (14) | 37 (24) | 15 (10) |
| Diarrhea | 12 (16) | 3 (4) | 9 (21) | 2 (5) | 28 (18) | 6 (4) |
| Fatigue | 12 (16) | 0 (0) | 11 (26) | 3 (7) | 27 (18) | 5 (3) |
| Hypophosphatemia | 6 (8) | 4 (5) | 6 (14) | 6 (14) | 13 (9) | 11 (7) |
| Elevated Alanine Aminotransferase | 2 (3) | 5 (7) | 2 (5) | 6 (14) | 4 (3) | 11 (7) |
| Elevated Aspartate Aminotransferase | 5 (7) | 3 (4) | 4 (9) | 3 (7) | 9 (6) | 6 (4) |
| Nausea | 6 (8) | 0 (0) | 11 (26) | 0 (0) | 21 (14) | 0 (0) |
| Muscle Spasms | 5 (7) | 0 (0) | 10 (23) | 0 (0) | 19 (13) | 0 (0) |
| Decreased Appetite | 8 (11) | 0 (0) | 7 (16) | 0 (0) | 17 (11) | 0 (0) |
| Vomiting | 5 (7) | 0 (0) | 6 (14) | 0 (0) | 15 (10) | 0 (0) |
| Blood Bilirubin Increased | 1 (1) | 1 (1) | 5 (12) | 0 (0) | 6 (4) | 1 (1) |

*Rash, Rash erythematous, Rash generalized, Rash macular, Rash maculo-papular, Rash papular, Rash pruritic, Urticaria, Drug rash with eosinophilia and systemic symptoms, Drug hypersensitivity, Adverse drug reaction.

Figure 3:
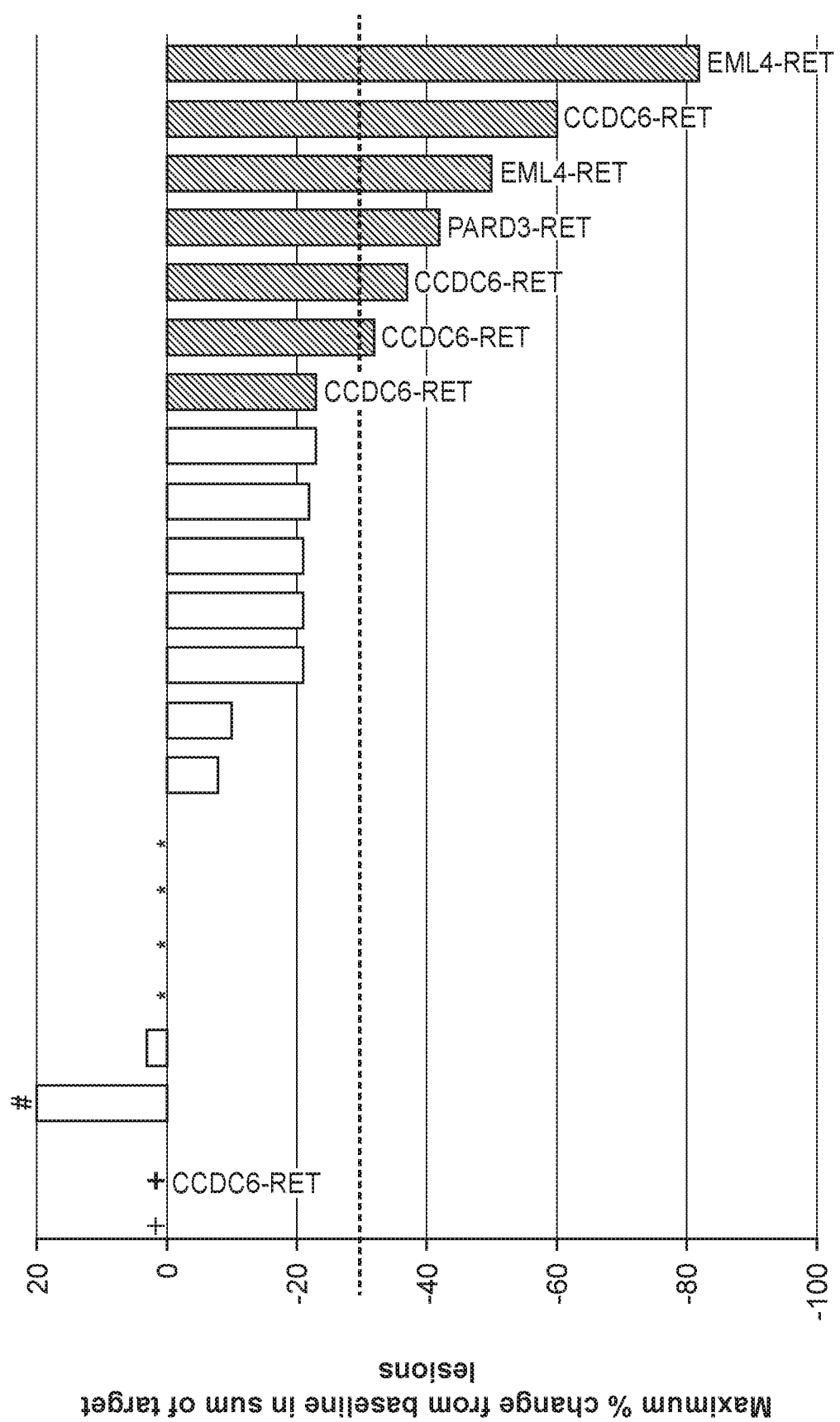
FIG. 3 is a waterfall plot demonstrating the anti-tumor activity of N-[3-[(6,7-dimethoxy-4-quinazolinyl)oxy]phenyl]-N'-[5-(2,2,2-trifluoro-1,1-dimethylethyl)-3-isoxazolyl]-urea in RET-inhibitor naïve, RET-fusion positive patients having non-small cell lung cancer (NSCLC). Each bar represents a single patient (total of 22 patients). The bars representing patients having a CCDC6-RET fusion, a PARD3-RET fusion or an EML4-RET fusion are labeled with the specific fusion. The remainder of the unlabeled bars represent patients having a KIF5B-RET fusion. The Y-axis represents the maximum percent change from baseline in the sum of target lesions.

FIG. 3 is a waterfall plot demonstrating the anti-tumor activity of N-[3-[(6,7-dimethoxy-4-quinazolinyl)oxy]phenyl]-N'-[5-(2,2,2-trifluoro-1,1-dimethylethyl)-3-isoxazolyl]-urea in RET-inhibitor naïve, RET-fusion positive patients having non-small cell lung cancer (NSCLC). Each bar represents a single patient (total of 22 patients). The bars representing patients having a CCDC6-RET fusion, a PARD3-RET fusion or an EML4-RET fusion are labeled with the specific fusion. The remainder of the unlabeled bars represent patients having a KIF5B-RET fusion. The Y-axis represents the maximum percent change from baseline in the sum of target lesions. Of the patients having non-KIF5B-RET fusions (n=8), 75% had a partial response. Of the patients having a KIF5-B-RET fusion (n=14), 3 has stable disease lasting 6 or more months. Additionally, a RET-inhibitor naïve patient having metastatic colorectal cancer having a CCDC6-RET fusion achieved a complete response and was continuing on study as of the data cut-off date of Aug. 1, 2017.

Conclusions from the study were as follows. N-[3-[(6,7-dimethoxy-4-quinazolinyl)oxy]phenyl]-N'-[5-(2,2,2-trifluoro-1,1-dimethylethyl)-3-isoxazolyl]-urea demonstrated a manageable safety profile in patients with advanced or metastatic solid tumors. Twenty two (22) RET fusion-positive, RET inhibitor-naïve NSCLC patients treated at the 275 mg or 350 mg once per day dose were evaluable for efficacy. Of these, 8 patients harbored RET fusions partners other than KIF5B, including CCDC6, EML4, and PARD3. The overall response rate (ORR) was 75% (95% CI: 34.9%-96.8%) in patients with non-KIF5B-RET fusions. Additionally, 1 patient had stable disease for about 6 treatment cycles. The median duration of response (DOR) in these patient had not been reached, with the longest DOR at 10.2 months. Of the other 14 patients harboring a KIF5B-RET fusion, none had a RECIST response, although 3 patients had stable disease lasting 6 or more months. This disparity in response between tumors with the KIF5B and non-KIF5B fusion partners is consistent with previous pooled efficacy evidence with other RET-active agents, suggesting that KIF5B-RET fusion may be less susceptible to targeted inhibition.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of treating a subject having cancer, the method comprising administering to said subject a therapeutically effective amount of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, wherein prior to said administration of said compound said subject is known to possess at least one genetic alteration in RET, wherein at least one genetic alteration in RET is a gene fusion selected from NCOA4-RET fusion, KIF5B-RET fusion, CCDC6-RET fusion, EML4-RET fusion, PARD3-RET fusion, and CLIP1-RET fusion and wherein said cancer in said subject is selected from colorectal cancer, lung cancer, non-small cell lung cancer, thyroid cancer, and medullary thyroid cancer.

2. The method according to claim 1, wherein said gene fusion is a CCDC6-RET fusion.

3. The method according to claim 1, wherein said gene fusion is an EML4-RET fusion.

4. The method according to claim 1, wherein said gene fusion is a PARD3-RET fusion.

5. The method according to claim 1, wherein said N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, is administered to said subject in amount of from about 100 mg to about 1000 mg per day.

6. The method according to claim 1, wherein said subject is RET-inhibitor naïve prior to the administration of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, to the subject.

7. The method according to claim 1, wherein said subject is not RET-inhibitor naïve prior to the administration of N-[3-[(6,7-dimethoxy-4-quinazolinyl)oxy]phenyl]-N'-[5-(2,2,2-trifluoro-1,1-dimethylethyl)-3-isoxazolyl]-urea, or a pharmaceutically acceptable salt thereof, to the subject.

8. The method according to claim 1, wherein said cancer in said subject is colorectal cancer.

9. The method according to claim 8, wherein said colorectal cancer is metastatic colorectal cancer.

10. The method according to claim 1, wherein said cancer in said subject is lung cancer.

11. The method according to claim 1, wherein said cancer in said subject is non-small cell lung cancer.

12. The method according to claim 1, wherein said cancer in said subject is thyroid cancer.

13. The method according to claim 1, wherein said cancer in said subject is medullary thyroid cancer.

* * * * *